Oct. 16, 1934. W. J. H. KORDES Plant Pat. 104
ROSE
Filed March 23, 1934
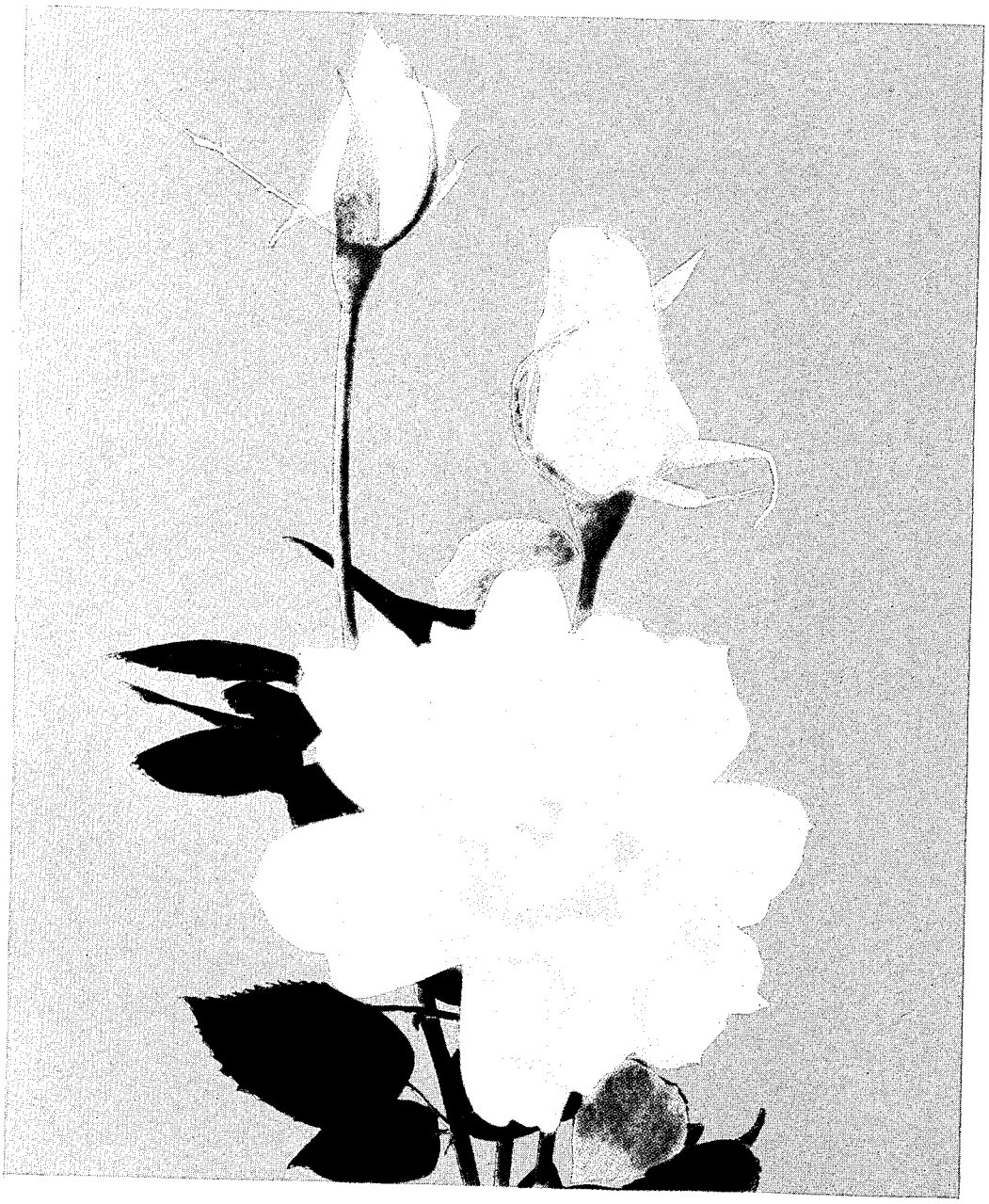
Inventor
Wilhelm John Henrich Kordes
By Orville M. Kile
Plant Patent Agent Patented Oct. 16, 1934

UNITED STATES PATENT OFFICE

104

ROSE

Wilhelm John Hinrich Kordes, Sparrieshoop, Germany, assignor to Henry A. Dreer, Incorporated, Philadelphia, Pa., a corporation of New Jersey Application March 23, 1934, Serial No. 717,101

1 Claim. (Cl. 47—61)

My new variety of rose is a hybrid tea. It was originated and developed by myself as a result of cross pollination. Its parents are the varieties Fontanelle x Julien Potin. The seedling first attracted my attention in 1931. It was first introduced to the public in Germany in the fall of 1933. This new variety presents new color tones and combinations, is well shaped in the bud and when fully opened the flower has long, twisted and curled petals which give it a decidedly unique appearance. The variety flowers freely and reproduces readily.

The accompanying illustration shows in full color two buds and a fully opened flower, as well as foliage and stems of this new variety.

The plant grows 4 to 4½ feet in height under ordinary favorable conditions; it makes a strong upright growth and is reasonably resistant to disease.

The stems are rather slender, light green, beset with a moderate number of reddish thorns of hooked form. The peduncles bear a moderate number of stiff hairs.

Leaflets of leaves on flowering stems are relatively small, ordinarily five in number. The leaves are forest green in color, slightly glossy, ovate, edges cut with numerous small serrations. The rachis usually bears one or two small thorns pointing downward.

The stipules are quite small and narrow but ending in sharp tips.

The hips are medium size and tapering.

The buds are medium size, medium length, well shaped and pointed.

The sepals are normally five in number, mostly medium length but with one or two on each flower measuring 1½ to 2 inches long, somewhat branched and foliaceous in character, with edges beset with coarse hairs widely spaced.

The flower is medium to large, double, having from 40 to 44 medium sized petals (in early December in greenhouses in the latitude of Philadelphia) and 8 to 10 small central petals. The petals have a novel habit of curling and rolling so that in its last stage the flower somewhat resembles a loosely rolled cactus dahlia. In its prime or fully opened stage the large outer petals are only slightly rolled but the central petals bend over and cover the center of the flower. The flower remains fresh on the bush for a long period and is long lasting when cut.

The blossoms are very sweet scented.

When grown as a forcing rose this new variety has a rich color, being a combination of orange, pink and yellow. The partly opened bud is predominantly pink, approximately "rose doree" (Ridgway's Color Standards and Nomenclature, edition 1912, Plate I), with even redder touches at the edges of the petals, but with much yellow and orange also showing. The fully opened flower, on the other hand, is predominantly yellow with shades of pink showing mainly on the edges of the petals. While the color may be popularly described as ochre-gold, the yellow coloring, according to Ridgway's Guide, ranges from "light orange yellow" on the portions of the petals farthest from the center, to "deep chrome" near the center (Ridgway's Color Standards and Nomenclature, Plate III). The pinks range from "rose doree" on the outer edges of the outer petals, to the lightest of pink where the color fades out.

Numerous yellow stamens, mounted by yellow anthers, and a medium number of pinkish pistils with white tops are almost entirely obscured from view by the overhanging or curving central petals.

Even richer colorings are found in this variety when grown out of doors.

Having thus disclosed my invention, I claim:

The variety of hybrid tea rose herein shown and described, characterized particularly by its rich orange, pink and yellowish coloring, the novel curling and bending of its petals, sweet scent and other desirable qualities.

WILHELM JOHN HINRICH KORDES.